United States Patent [19]
Waldron

[11] Patent Number: 5,887,286
[45] Date of Patent: Mar. 30, 1999

[54] EAR PROTECTOR

[76] Inventor: Carolyn A. Waldron, 3005 S. 76th St., Tampa, Fla. 33619-6423

[21] Appl. No.: 10,755

[22] Filed: Jan. 22, 1998

[51] Int. Cl.⁶ .................................................. H04R 25/00
[52] U.S. Cl. .............................. 2/209; 181/129; 381/370; 455/347; 455/568
[58] Field of Search ................................. 181/129; 2/209, 2/203, 208, 423, 455; 381/370, 371, 376, 309; 455/351, 350, 347, 568, 569, 575, 90

[56] References Cited

U.S. PATENT DOCUMENTS

| | | | |
|---|---|---|---|
| 1,988,880 | 10/1935 | Strouse | 128/152 |
| 3,311,921 | 4/1967 | Helm | 2/3 |
| 4,465,159 | 8/1984 | Stallings | 181/129 |
| 4,565,258 | 1/1986 | Butler et al. | 181/129 |
| 5,018,599 | 5/1991 | Dohi et al. | 181/129 |
| 5,146,619 | 9/1992 | Brown | 455/351 |
| 5,519,783 | 5/1996 | Kumar | 381/183 |
| 5,640,458 | 6/1997 | Nishiguchi et al. | 381/74 |

Primary Examiner—Michael A. Neas
Assistant Examiner—Tejash D. Patel

[57] ABSTRACT

A child ear protector is provided including a pair of ear enclosures each defining an interior space and a free peripheral edge. Each enclosure has an elastomeric gasket formed about the free peripheral edge thereof. A resilient head set is included having a pair of ends mounted to the ear enclosures to maintain the same over ears of the user during use. A music mechanism is situated within at least one of the ear enclosures for transmitting a melody.

5 Claims, 2 Drawing Sheets

EAR PROTECTOR

BACKGROUND OF THE INVENTION

1. Field of the Invention

The present invention relates to headphones and more particularly pertains to a new ear protector for protecting ears of a child and further providing a soothing affect during bathing.

2. Description of the Prior Art

The use of headphones is known in the prior art. More specifically, headphones heretofore devised and utilized are known to consist basically of familiar, expected and obvious structural configurations, notwithstanding the myriad of designs encompassed by the crowded prior art which have been developed for the fulfillment of countless objectives and requirements.

Known prior art headphones include U.S. Pat. No. 4,727,599; U.S. Pat. No. 4,864,619; U.S. Pat. No. Des. 342,071; U.S. Pat. No. Des. 340,454; U.S. Pat. No. Des. 291,197; and U.S. Pat. No. 4,683,587.

In these respects, the ear protector according to the present invention substantially departs from the conventional concepts and designs of the prior art, and in so doing provides an apparatus primarily developed for the purpose of protecting ears of a child and further providing a soothing affect during bathing.

SUMMARY OF THE INVENTION

In view of the foregoing disadvantages inherent in the known types of headphones now present in the prior art, the present invention provides a new ear protector construction wherein the same can be utilized for protecting ears of a child and further providing a soothing affect during bathing.

The general purpose of the present invention, which will be described subsequently in greater detail, is to provide a new ear protector apparatus and method which has many of the advantages of the headphones mentioned heretofore and many novel features that result in a new ear protector which is not anticipated, rendered obvious, suggested, or even implied by any of the prior art headphones, either alone or in any combination thereof.

To attain this, the present invention generally comprises a pair of closed ear enclosures each with a circular face. A cylindrical periphery is integrally coupled to a peripheral edge of the circular face and extends outwardly therefrom to define an interior space and a free peripheral edge. The circular face of each enclosure has a pair of sleeves defining a pair of rectangular slots which are aligned along an axis. A snap is mounted below the sleeves on the axis. An elastomeric gasket is formed about the free peripheral edge for reasons that will become apparent hereinafter. To define a compartment with the circular face, an inner divider defined by a portion of a sphere is mounted within the interior space of each ear enclosure. As shown in FIG. 4, the inner divider has a plurality of annularly aligned apertures formed therein. Next provided is a resilient head set having an inverted V-shaped configuration, as shown in FIG. 1. The head set has an inner surface lined with an elastomeric material. The head set further includes a pair of upturned ends. A plurality of undulations are formed in an outer source of the head set adjacent the ends. During use, the ends of the head set are each situated through the slots of the sleeves of an associated one of the ear enclosures. This allows the head set to be worn on a head of a user such that the ear enclosures encompass ears of the user. As such, the extent in which the ends of the head set extend through the slots of the sleeve may be adjusted to conform to heads of various sizes. FIG. 1 shows a flexible elastic chin strap having an elongated rectangular configuration. A pair of ends of the chin strap are each equipped with a button for releasably engaging the snap of a corresponding ear enclosure. As such, the chin strap encompasses a chin of the user thereby maintaining the headset on the user's head. Lastly, music means is situated within at least one of the ear enclosures for transmitting sound through the apertures formed in the inner divider.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new ear protector apparatus and method which has many of the advantages of the headphones mentioned heretofore and many novel features that result in a new ear protector which is not anticipated, rendered obvious, suggested, or even implied by any of the prior art headphones, either alone or in any combination thereof.

It is another object of the present invention to provide a new ear protector which may be easily and efficiently manufactured and marketed.

It is a further object of the present invention to provide a new ear protector which is of a durable and reliable construction.

An even further object of the present invention is to provide a new ear protector which is susceptible of a low cost of manufacture with regard to both materials and labor, and which accordingly is then susceptible of low prices of sale to the consuming public, thereby making such ear protector economically available to the buying public.

Still yet another object of the present invention is to provide a new ear protector which provides in the apparatuses and methods of the prior art some of the advantages thereof, while simultaneously overcoming some of the disadvantages normally associated therewith.

Still another object of the present invention is to provide a new ear protector for protecting ears of a child and further providing a soothing affect during bathing.

Even still another object of the present invention is to provide a new ear protector that includes a pair of ear enclosures each defining an interior space and a free peripheral edge. Each enclosure has an elastomeric gasket formed about the free peripheral edge thereof. A resilient head set is included having a pair of ends mounted to the ear enclosures to maintain the same over ears of the user during use. A music mechanism is situated within at least one of the ear enclosures for transmitting a melody.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
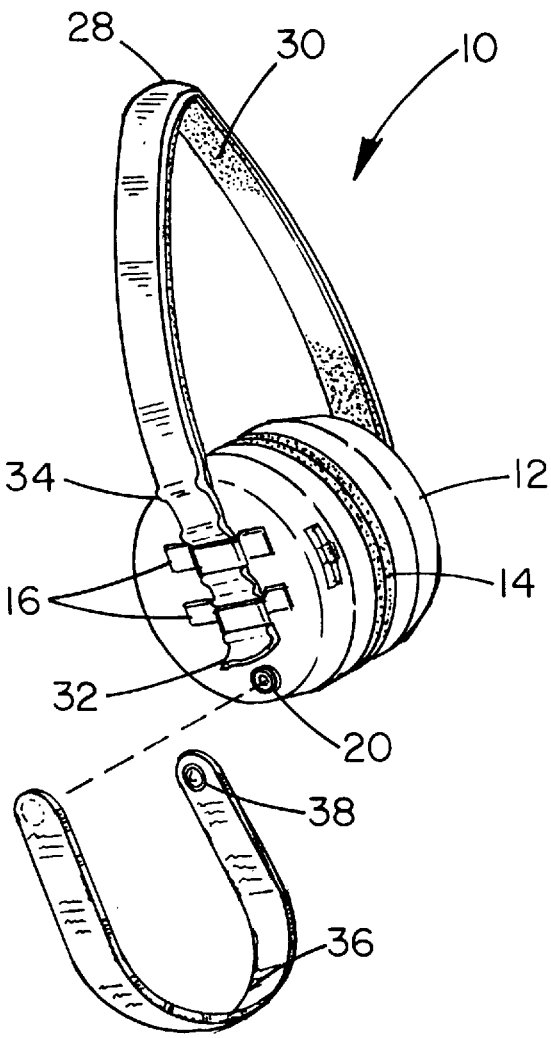
FIG. 1 is a perspective view of a new ear protector according to the present invention.
Figure 2:
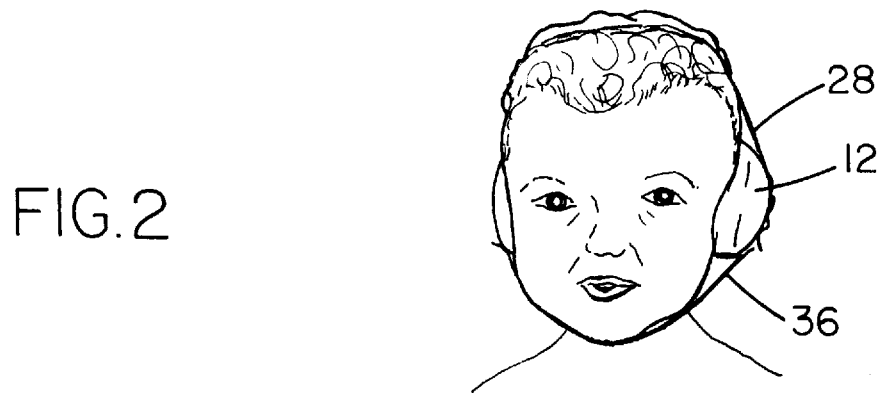
FIG. 2 is a front view of the present invention.
Figure 3:
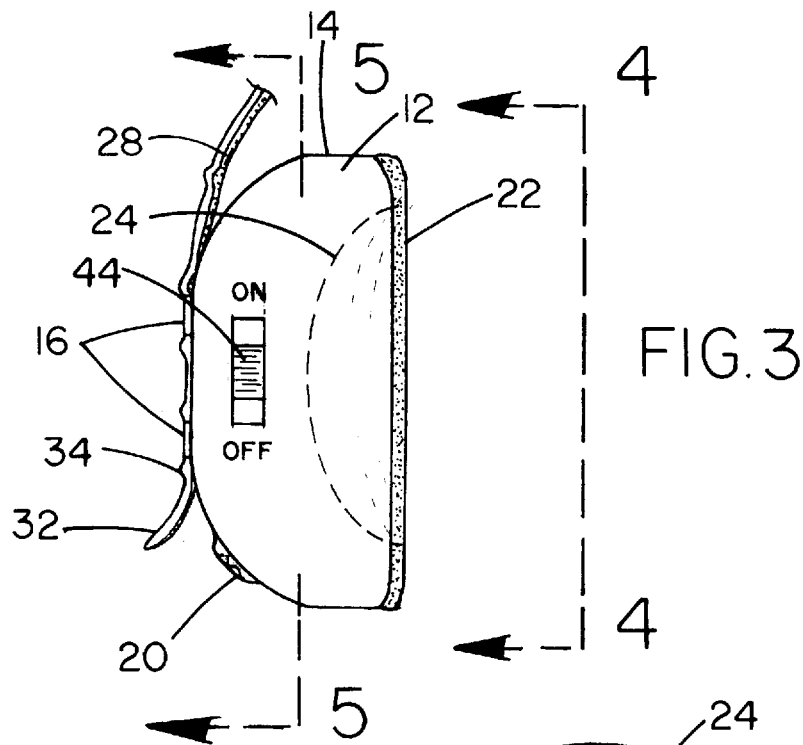
FIG. 3 is a side view of the present invention.

With reference now to the drawings, and in particular to FIGS. 1 through 5 thereof, a new ear protector embodying the principles and concepts of the present invention and generally designated by the reference numeral 10 will be described.

Figure 4:
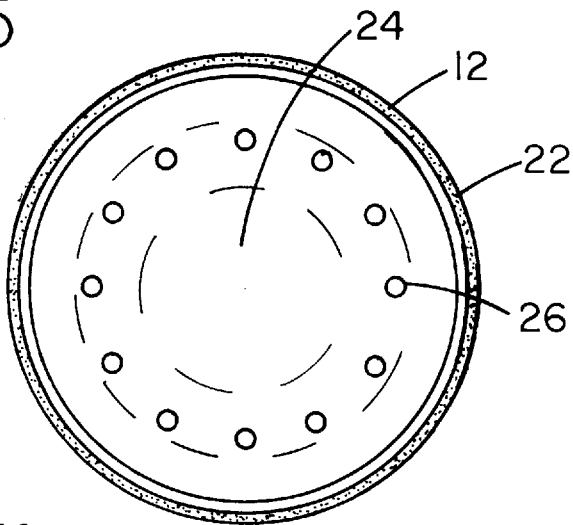
FIG. 4 is an inside view of one of the ear enclosures of the present invention.

The present invention, as designated as numeral 10, includes a pair of closed ear enclosures 12 each with a circular face. A cylindrical periphery 14 is integrally coupled to a peripheral edge of the circular face and extends outwardly therefrom to define an interior space and a free peripheral edge. The circular face of each enclosure has a pair of sleeves 16 defining a pair of rectangular slots which are aligned along an axis. A snap 20 is mounted below the sleeves on the axis. An elastomeric gasket 22 is formed about the entire free peripheral edge for reasons that will become apparent hereinafter. To form a compartment with the circular face, an inner divider 24 defined by a portion of a sphere is mounted within the interior space of each ear enclosure. As shown in FIG. 4, the inner divider has a plurality of annularly aligned apertures 26 formed therein. The inner divider is preferably formed of an elastomeric material.

Next provided is a resilient head set 28 having an inverted V-shaped configuration, as shown in FIG. 1. The head set has an inner surface lined with an elastomeric material 30. The head set further includes a pair of upturned ends 32. A plurality of undulations 34 are formed in an outer source of the head set adjacent the ends.

During use, the ends of the head set are each situated through the slots of the sleeves of an associated one of the ear enclosures. This allows the head set to be worn on a head of a user such that the ear enclosures encompass his or her ears. As such, the extent in which the ends of the head set extend through the slots of the sleeve may be adjusted to conform to heads of various sizes. Such adjustment is accomplished by an undulation being slid between the sleeves one at a time thereby allowing the adjustment of the head set between various discrete lengths.

FIG. 1 shows a flexible elastic chin strap 36 having an elongated rectangular configuration. A pair of ends of the chin strap are each equipped with a button 38 for releasably engaging the snap of a corresponding ear enclosure. The chin strap thus encompasses a chin of the user thereby maintaining the headset on the user's head.

Figure 5:
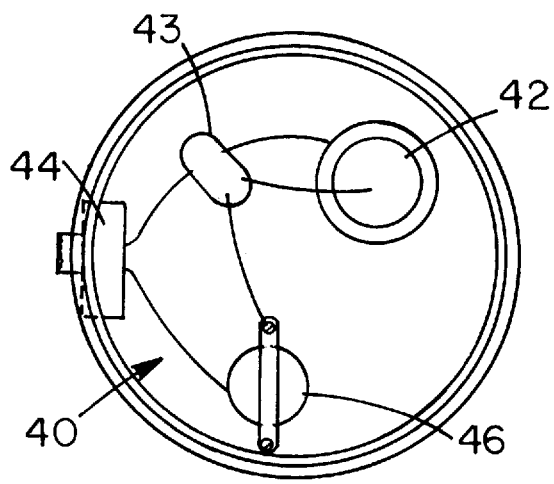
FIG. 5 is a cross-sectional view of the present invention taken along line 5—5 shown in FIG. 3.

Lastly, music means 40 is situated within at least one of the ear enclosures for transmitting sound through the apertures formed in the inner divider. As shown in FIG. 5, the music means comprises a piezo electric sound device 42 coupled to an integrated circuit 43 for producing a single continuous melody upon the actuation thereof. A switch 44 is mounted on the periphery of one of the ear enclosures and is further electrically connected between the integrated circuit and a battery 46.

Preferably, the switch is equipped with a gasket for precluding the entry of water into the compartment of the associated ear enclosure. It should be noted that all of the components of the music means are situated within the compartment of the designated ear enclosure. As an option, a wire may be run through the head set and connected to another sound device situated within the other ear enclosure for effecting a stereo affect. During use, the music means functions to relax a child during bathing.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A child ear protector comprising, in combination:
   a pair of closed ear enclosures each including a circular face and a cylindrical periphery integrally coupled to a peripheral edge thereof and extending outwardly therefrom to define an interior space and a free peripheral edge, the circular face of each enclosure having a pair of sleeves defining a pair of rectangular slots which are aligned along an axis, a snap mounted below the sleeves on the axis, an elastomeric gasket formed about the free peripheral edge, and an inner divider defined by a portion of a sphere mounted within the interior space of each ear enclosure and protruding inwardly to define a compartment with the circular face, the inner divider having a plurality of annularly aligned apertures formed therein;

a resilient head set having an inverted V-shaped configuration with an inner surface lined with an elastomeric material, the head set including a pair of upturned ends which extend outwardly and a plurality of undulations formed in an outer surface of the head set adjacent the ends, the ends of the head set are each situated through the slots of the sleeves of an associated one of the ear enclosures for being slidably positioned to adjust the head set between discrete lengths so that the ear protector may be worn on a head of a user such that the ear enclosures encompass ears of the user, whereby the extent in which the ends of the head set extend through the slots of the sleeve may be adjusted to conform to heads of various sizes;

a flexible elastic chin strap having an elongated rectangular configuration for encompassing a chin of the user to thereby securely maintain the head set on the head of the user, the chin strap having a pair of ends each equipped with a button for releasably engaging the snap of a corresponding ear enclosure such that the chin strap may be partially released from the head set for placement on and removal from the head of the user and may be completely removed from the head set when securing is not needed; and music means situated within one of the ear enclosures for transmitting sound through the apertures formed in the inner divider, the music means including a piezo electric sound device coupled to an integrated circuit for producing a single continuous melody upon the actuation thereof and a switch mounted on the periphery of one of the ear enclosures and further electrically connected between the integrated circuit and a battery for selectively actuating the integrated circuit, wherein the switch has a gasket for precluding the entry of water into the compartment of the associated ear enclosure.

2. A child ear protector comprising:

a pair of closed ear enclosures each defining an interior space and a free peripheral edge, each enclosure having an elastomeric gasket formed about the free peripheral edge and an inner divider generally defined by a portion of a sphere mounted within the interior space of each ear enclosure and protruding inwardly to define a compartment, each ear enclosure having a pair of sleeves defining a pair of slots which are aligned along an axis;

a resilient head set having a pair of ends mounted to the ear enclosures to maintain the same over ears of the user, the head set including a pair of upturned ends which extend outwardly and a plurality of undulations formed in an outer surface of the head set adjacent the ends for being slidably positioned through the sleeves of the ear enclosures to adjust the head set between discrete lengths; and music means situated within at least one of the ear enclosures for transmitting audio signals, the music means including a sound device for producing a single continuous melody upon the actuation thereof via a switch mounted on one of the ear enclosures.

3. A child ear protector as set forth in claim 2 wherein a first coupling means is mounted below the sleeves and a chin strap is included having an elongated configuration with a pair of ends each equipped with a second coupling means for releasably securing with the first coupling means of a corresponding ear enclosure such that the chin strap encompasses a chin of the user thereby maintaining the headset on the head of the user.

4. A child ear protector as set forth in claim 3 wherein the chin strap is flexible and elastic.

5. A child ear protector as set forth in claim 2 wherein the switch has a gasket for precluding the entry of water into the compartment of the associated ear enclosure.

\* \* \* \* \*